United States Patent [19]

Bland

[11] Patent Number: 5,383,885

[45] Date of Patent: Jan. 24, 1995

[54] BLOOD COLLECTION AND TESTING DEVICE

[76] Inventor: Todd A. Bland, 4301 Abbott Rd., Lincoln, Nebr. 68516

[21] Appl. No.: 82,950

[22] Filed: Jun. 29, 1993

[51] Int. Cl.$^6$ ............................................. A61B 17/32
[52] U.S. Cl. .................................................... 606/182
[58] Field of Search ......................... 128/760, 763, 771; 606/181, 182

[56] References Cited

U.S. PATENT DOCUMENTS

| | | | |
|---|---|---|---|
| 3,741,197 | 6/1973 | Saz et al. | 60/182 |
| 4,388,925 | 6/1983 | Burns | 606/182 |
| 5,014,718 | 5/1991 | Mitchen | 606/181 |
| 5,201,324 | 4/1993 | Swierczek | 606/182 |

FOREIGN PATENT DOCUMENTS 3060645 3/1991 Japan ................................. 128/763

Primary Examiner—Max Hindenburg
Attorney, Agent, or Firm—George R. Nimmer

[57] ABSTRACT

Described is a blood collection and testing device including a hollow housing surrounding a vertical axis and having horizontally disposed: an upper annular end; a larger, lower annular end equipped with gauze adapted to receive a blood sample; a circular membrane located above the lower annular end and centrally provided with a puncturably rupturable bubble containing a chemical reagent reactable with human blood; and a centrally-perforate wall located in-between the circular membrane and the housing upper annular end. Slidably disposed within the housing upper annular end is a pushbutton provided with a needle extending along the vertical axis and adapted to puncturably rupture the circular membrane bubble as the slidable pushbutton moves along the vertical axis. A resiliently yieldable helical spring surrounds the needle and bears between the centrally-perforate wall and the pushbutton.

2 Claims, 3 Drawing Sheets 5,383,885

BLOOD COLLECTION AND TESTING DEVICE

BACKGROUND OF THE INVENTION

Generally recognized is a need for easily, quickly, reliably, and economically testing human subjects blood as indication of the subject's physiological health and-/or possible presence of a pathological malady. The public is increasingly exhibiting profound interest in blood collection and testing devices that will easily, quickly, reliably, and economically test the human blood as indication of general physiological health and of the possible presence of pathological disorders such as tuberculosis, hepatitis, AIDS, etc.

1. Objectives of the Invention

It is accordingly the general objective of the present invention to provide an easy, quick, reliable, and economical blood collection and testing device that enables medical professionals, as well as the general citizenry, to test their patients, themselves, family members, and potential sexual partners for general physical health and for the possible presence of transmittable pathological diseases such as tuberculosis, hepatitis, AIDS, etc.

2. General Statement of the Invention

With the aforementioned general objectives in view, and together with other ancillary and related specific objectives which will become more apparent as this description proreeds, the blood collection and testing device of the present invention generally comprises: a hollow housing surrounding a vertical-axis and having the following horizontally extending portions and augmentations: an upper annular end; a larger, lower annular end that is augmentally equipped with gauze adapted to receive a human blood samples a circular membrane located above the lower annular end and centrally provided with a puncturably rupturable bubble containing a chemical reagent reactable with human blood; and a centrally-perforate wall located in-between the circular membrane and the housing upper annular end. Slidably disposed within the housing at its upper annular end is a pushbutton provided with a depending needle extending along the vertical axis and adapted to puncturably rupture the circular membrane bubble as the slidable pushbutton moves along the vertical axis, whereby the bubble's chemical reagent gravitationally flows toward and reacts with human blood at the gauze layer A resiliently yieldable spring means, such as a helical spring, bearing between the centrally-perforate wall and the pushbutton, normally maintains the needle away from the central membrane bubble portion.

BRIEF DESCRIPTION OF THE DRAWING

In the drawing, wherein like characters refer to like parts in the several views, and in which.

DETAILED DESCRIPTION OF THE DRAWING

Figure 1:
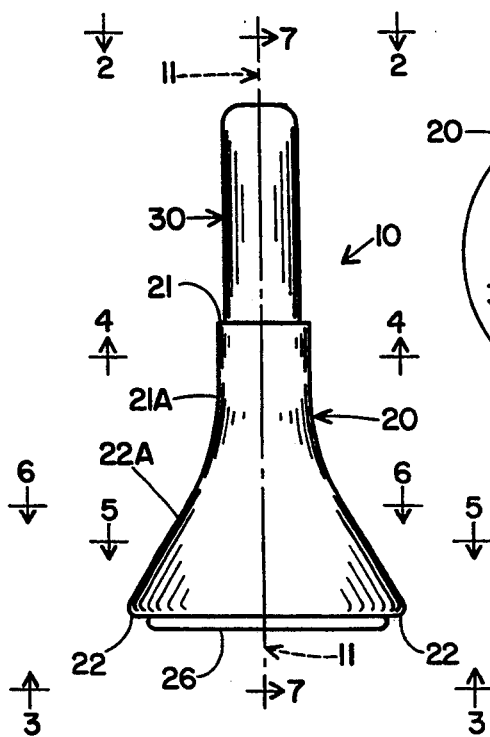
FIG. 1 is a typical side elevational view of a representative embodiment (10) of the "Blood Collection and Testing Device" of the present invention.
Figure 2:
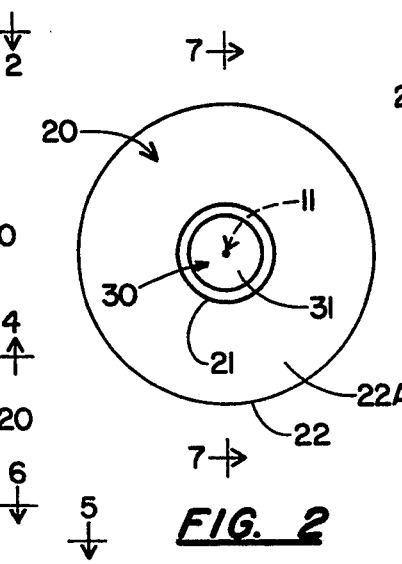
FIG. 2 is a top plan view of the FIG. 1 embodiment.
Figure 3:
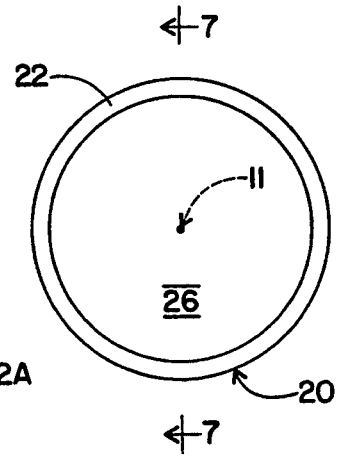
FIG. 3 is a bottom I plan view of the FIG. 1 embodiment.
Figure 4:
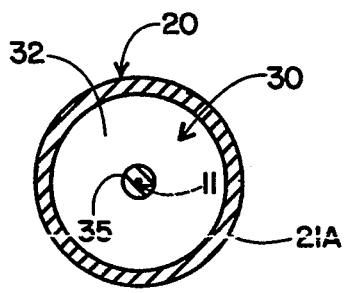
FIG. 4 is a sectional plan view taken along line 4—4 of FIG. 1.
Figure 5:
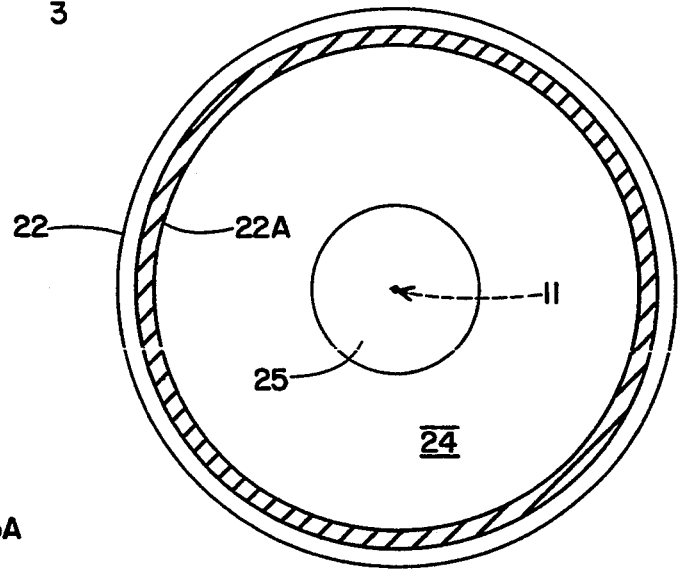
FIG. 5 is a sectional plan view taken along line 5—5 of FIGS. 1, 7, and 8.
Figure 6:
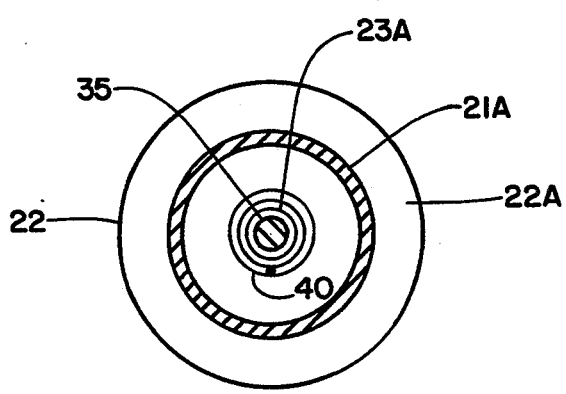
FIG. 6 is a sectional plan view taken along lines 6—6 of FIGS. 1, 7, and 8.
Figure 7:
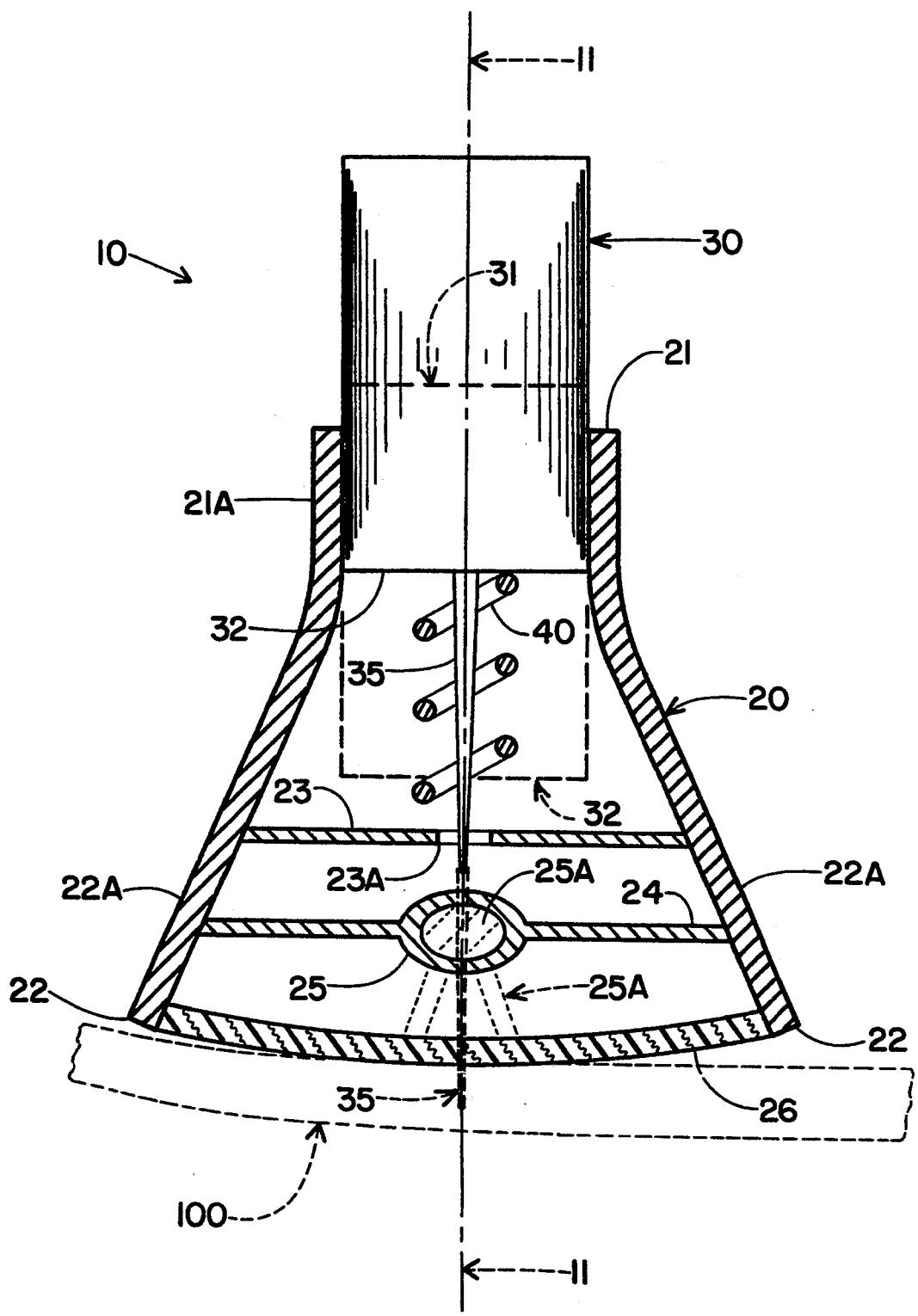
FIG. 7 is a sectional elevational view taken along lines 7—7 of FIGS. 1, 2, and 3.

Turning initially to drawing FIGS. 1-7 which depict representative embodiment 10 of the "Blood Collection and Testing Device", and which embodiment 10 generally comprises: a hollow housing 20 surrounding a vertical axis a pushbutton 30 having a depending needle 35 that are together co-reciprocatable along vertical axis 11 whereby needle 35 is adapted to puncture therebelow a bubble-like encapsulated supply (25) of a chemical reagent fluid 25A that is thence downwardly flowable to a laminar gauze 26 located at housing lower annular end 22; and spring means (e.g. 40) resiliently bearing between the pushbutton 3O and a centrally-perforate interior wall 23 for housing 20. Laminar gauze layer 26 is adapted to receive a human blood sample that is chemically interreactable with a said reagent fluid 25A.

Hollow housing 20 has a pair of annular (and preferably circularly annular) terminal ends that respectively directionally horizontally transversely and perpendicularly intersect vertical axis 11, including an upper annular end 21 and a dimensionally larger lower annular end 22. Accordingly, housing 20 has an upper-length 21A circularly tubularly surrounding upper annular end 21 and a lower-length 22A converging upwardly from lower annular end 22 to merge at a housing first intermediate location with said upper-length 21A. Housing 20 at lower annular end 22 is augmented with said attached laminar gauze layer which is permeable to a said downwardly releasable chemical reagent fluid 25A as well as receptive to a human blood sample. Housing lower-length 22A, at a second intermediate location between said first intermediate location and said annular lower end 22, is provided with a horizontally extending and peripherally attached circular membrane (24) including a centrally located and puncturably rupturable bubble-portion (25) encapsulating a needle-puncturable supply of chemical reagent fluid (25A) of a type that chemically reacts with a human blood sample at gauze layer 26. In-between said circular membrane 24 and said pushbuttom 30 at a bottom end 32 therefor, hollow housing 20 is provided with a centrally-perforate (23A) wall 23 that perpendicularly intersects vertical axis 11.

Manually downwardly depressible pushbutton 30 is slidably surrounded by housing upper-length 21A including at annular upper end 21, pushbutton 30 having a top end 31, a said bottom end 32, and being augmentally provided with a needle depending from bottom end 32 along vertical axis 11. There are spring means (e.g. 40, 90) for resiliently biasing the pushbutton (30) and its needle (35) upwardly away from said encapsulated source of chemical reagent fluid (25A). For example, such spring means might be a helical spring (40, 90) surrounding vertical axis 11 and needle 35 and being between centrally-perforate wall 23 and the pushbutton bottom end 32.

Figure 8:
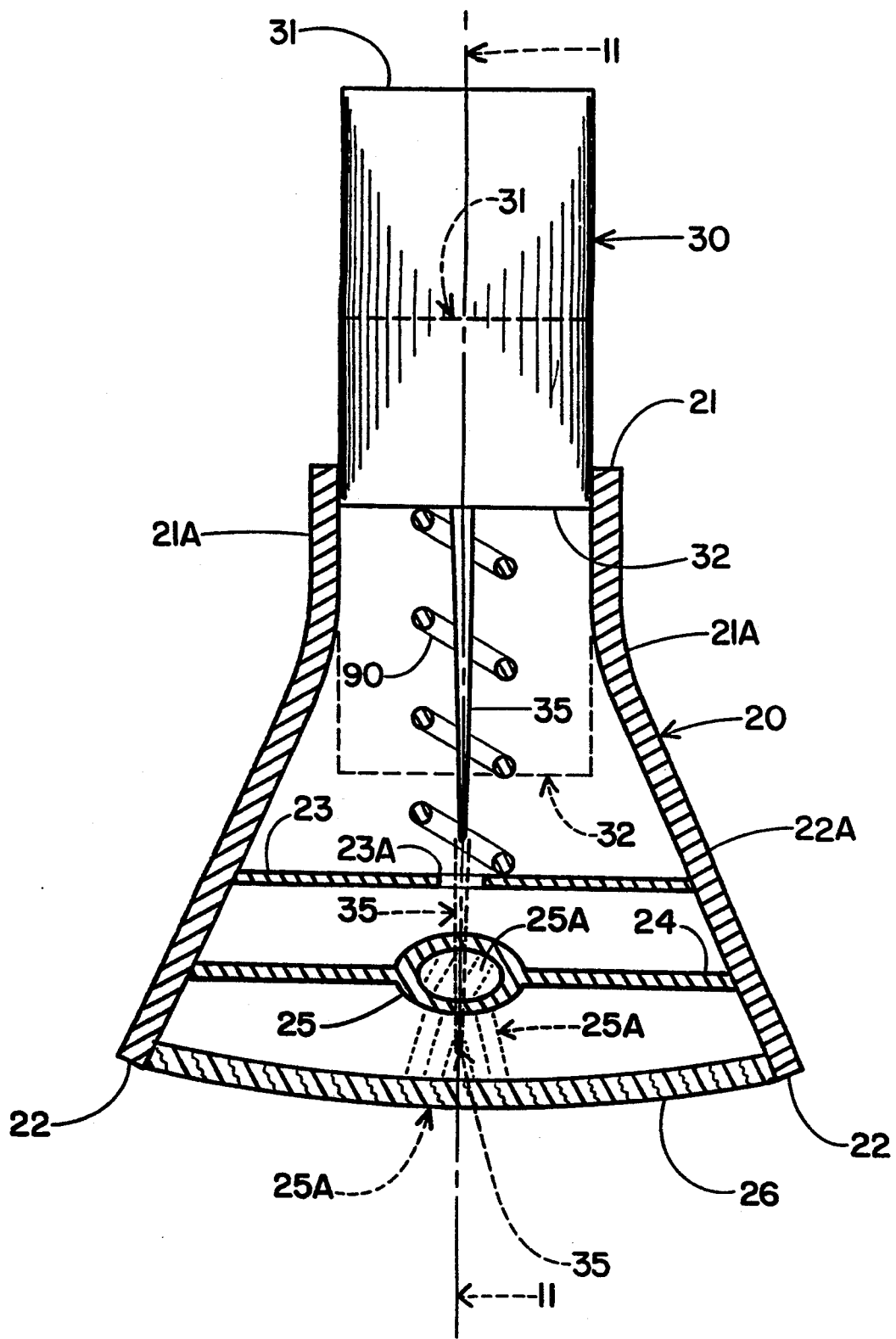
FIG. 8 is a sectional elevational view akin to FIG. 7, but showing an alternate embodiment (80) of the "Blood Collection and Testing Device" of the present invention.

Introduction of the human subject's blood sample, at the "Blood Collection and Testing Device" gauze layer, and thereat for chemical reaction with puncturably-released reagent fluid 25A, can be accomplished by either of two alternate methods. In the first method, and as suggested in drawing FIG. 7, the spring means (40) is sufficiently yieldable along vertical axis 11 to permit movable needle 35 to puncture both the central membrane's central capsule 25 and the subject's capillaried skin (100), positioned at gauze layer 26, whereby the puncturably-released chemical reagent fluid 25A and the human subject's blood (100) will thereby immediately react at the gauze layer 26. In the second method, and as suggested in drawing FIG. 8, the spring means (90) is barely sufficiently yieldable along vertical axis 11 to puncturably rupture only the encapsulated (25) chemical reagent fluid (25A) but not the laminar gauze 26. Thus, in the FIG. 8 mode, the tested human subject introduces his/her blood sample (100) by means independent of needle 35 to gauze layer 26. Such "means independent of needle 35" might be in the form of a secondary-needle (not shown) that extends upwardly from the pushbutton top end 31 along vertical axis 11.

A protective cap (not shown) might be removably provided across the housing lower annular end 22 ancillary to initial and test-following usages of the "blood collection and testing device".

From the foregoing, the construction and operation of the "blood collection and testing device" concept will be readily understood and further explanation is believed to be unnecessary. However, since numerous modifications and changes will readily occur to those skilled in the art, it is not desired to limit the invention to the exact constructions shown and described, and accordingly, all suitable modifications and changes and equivalents may be resorted to, and falling within the scope of the appended claims.

I claim:

1. A blood collection and testing device comprising:
   a hollow housing symmetrically disposed about a vertical axis, said housing having an upper annular end and a lower annular end wherein both ends lie in planes perpendicular to said vertical axis, said housing having an upper tubular portion extending from said upper end to a first intermediate location in-between said upper and lower ends and a lower conical portion extending from said first intermediate location to said lower end and wherein said lower annular end has a larger diameter than said upper annular end;
   a circular fluid-pervious gauze attached peripherally to said housing lower annular end and extending across said lower end, said gauze being adapted to receive a sample of blood;
   a circular membrane attached peripherally to said hollow housing at a second intermediate location in-between said first intermediate location and said lower end, said membrane including a centrally located and puncturably rupturable bubble portion containing a fluid reagent of a type that reacts with human blood;
   a pushbutton slidable within said hollow housing and translatable along said vertical axis between an extended position and a retracted position, said pushbutton being dimensioned and configured to slidably engage the substantial entirety of the inner surface of the said hollow housing upper portion, said pushbutton including a top end located above the hollow housing upper end and a bottom end located at said first intermediate location when said pushbutton is in said retracted position and located between said first and second intermediate locations when said pushbutton is in said extended position;
   a needle extending downwardly from the bottom end of said pushbutton and generally lying along said vertical axis, said needle being of a length such that it lies between said first and second intermediate locations in said pushbutton retracted position and such that it extends below said hollow housing lower end in said pushbutton extended position, whereby said puncturably rupturable bubble is puncturably rupturable by said needle as said pushbutton is moved from said retracted position to said extended position and whereby also said fluid reagent flows toward the gauze and chemically interacts with human blood at said gauze; and
   means for biasing said pushbutton toward said retracted position.

2. The blood collection and testing device of claim 1 wherein the hollow housing in-between said circular membrane and said pushbutton bottom end is provided with a centrally-perforate wall that perpendicularly intersects and surrounds said vertical axis; and wherein the means for biasing said pushbutton toward said retracted position comprises a helical spring surrounding said needle and resiliently bearing between said pushbutton bottom end and said centrally-perforate wall.

* * * * *